… …

United States Patent [19]
de la Veaux

[11] Patent Number: 5,237,875
[45] Date of Patent: Aug. 24, 1993

[54] METAL FATIGUE DETECTOR

[75] Inventor: Raymond C. de la Veaux, Sarasota, Fla.

[73] Assignee: Tensiodyne Corporation, Los Angeles, Calif.

[21] Appl. No.: 677,163

[22] Filed: Mar. 29, 1991

[51] Int. Cl.$^5$ .............................................. G01B 7/16
[52] U.S. Cl. .................................... 73/775; 73/862.68
[58] Field of Search ............. 73/762, 775, 767, 862.68

[56] References Cited

U.S. PATENT DOCUMENTS

| | | | |
|---|---|---|---|
| 3,136,154 | 6/1964 | Christensen | 73/775 X |
| 3,596,269 | 7/1971 | Laska | 73/775 X |
| 3,782,178 | 1/1974 | Thomas | 73/767 X |
| 3,786,679 | 1/1974 | Crites | 73/775 X |
| 3,979,949 | 9/1976 | Smith | 73/762 X |
| 4,590,804 | 5/1986 | Brull | 73/762 |
| 4,639,997 | 2/1987 | Brull | 29/407 |

Primary Examiner—Jerry W. Myracle
Attorney, Agent, or Firm—Sprung, Horn, Kramer & Woods

[57] ABSTRACT

A device for detecting fatigue of a monitored structure due to flexure comprises a fuse made of the same material as the monitored structure and formed with a failure portion designed to fail because of fatigue prior to failure of the monitored structure when the fuse and the monitored structure both experience the same stress history. An adhesive secures the fuse to the monitored structure and extends substantially over the entirety of a side of the fuse that is adjacent to the monitored structure. However, the adhesive is spaced apart from the failure portion. The adhesive ensures that the fuse and the monitored structure experience substantially the same stress history in both tension and compression yet does not inhibit failure of the failure portion. The device can be monitored locally by sight or can be used as part of a remote-monitoring system.

16 Claims, 4 Drawing Sheets

METAL FATIGUE DETECTOR

BACKGROUND OF THE INVENTION

1. Field of the Invention

This invention relates to fatigue monitors and more particularly to a novel and highly effective device for detecting fatigue of a monitored structure due to flexure and to a method of applying the device to the monitored structure. The invention is applicable particularly to the detection of metal fatigue but is applicable also to the detection of fatigue in other structural materials.

2. Description of the Prior Art

U.S. patents to Maurice A. Brull U.S. Pat. No. 4,590,804 and U.S. Pat. No. 4,639,997, both assigned to the assignee of the present invention, disclose respectively a device for and method of monitoring fatigue life. The patents illustrate what are called coupons, otherwise known as fatigue fuses, arranged in a row and each having different notch patterns ranging from the mildest notch pattern to the most aggressive notch pattern. The coupons will fail because of fatigue in a prescribed sequence. The number of load cycles to failure as a function of stress amplitude for the different coupons can be plotted, and as each coupon fails, it gives an indication of the remaining life expectancy of the monitored structure.

More particularly, each of the coupons includes a special notch pattern comprising at least one pair of notches designed to produce a local stress concentration. One notch of each of the notch pairs is disposed on each of the longitudinal sides of the coupon, the notches of the notch pair being substantially geometrically the same. Their axis must be oriented along a suitably chosen direction. The notch pattern of each of the coupons produces a stress field which varies in intensity from relatively mild to very severe. The severity of the local stress field is controlled by the geometry of the notch pattern. Smooth geometries produce a mild stress concentration, while geometric discontinuities produce severe stresses. In this manner, if all of the coupons can be subjected to the same stress history, it will result in the development of different stress concentrations in the region of the notch tips of each coupon, so that each coupon will have a different fatigue life. Moreover, if the stress history of the coupons is the same as that of the monitored structure, the fatigue life of each coupon will be a different predetermined percentage of the fatigue life of the monitored structure.

In accordance with the disclosures of the patents, the coupons are secured to the monitored structure by pins, adhesive or spot welding so that, ideally, all of the coupons experience the same strain history as the monitored structure.

It has now been discovered that the mounting techniques of the prior art, while producing good results in certain circumstances, fail to produce optimum results under other circumstances. In particular, the mounting techniques of the prior art fail to ensure that the coupons experience the same stress history as the monitored structure. The discrepancy between the stress history of the coupons and that of the monitored structure is particularly large in the case of compressive stresses.

This has practical consequences because, in many typical cases, the monitored structure will undergo stresses that alternately produce tension and compression, as illustrated in FIG. 1.

If the fuse is not subjected to compressive stresses to the same extent as the monitored structure, the fuse will not fail when it ideally should in view of the predetermined notches formed in it. In response to a compressive stress, a given fuse mounted in accordance with the prior art may bend out or in at the notches and will thus fail unpredictably. A coupon designed to fail at, say, 50% of the fatigue life of the monitored structure may actually survive intact until failure of the monitored structure, thereby giving no warning at all.

Moreover, the prior fuse is not adapted for incorporation in a remote-monitoring system. Remote monitoring is very important where the monitored structure is not readily accessible for inspection. In modern aircraft, for example, there are vital structural components deeply recessed in cavities that are stuffed with electrical leads and components, hydraulic lines, and other elements that render access for visual inspection time-consuming, difficult and expensive.

OBJECTS AND SUMMARY OF THE INVENTION

An object of the invention is to remedy the problems of the prior art noted above by providing a fatigue monitor that more reliably gives warning of impending failure of a monitored structure In particular, an object of the invention is to provide a fatigue monitor applied to a monitored structure in such a manner as more faithfully to mirror the stress history of the monitored structure, especially in compression.

Another object of the invention is to provide a fatigue monitor that is adapted for incorporation in a remote-monitoring system.

The foregoing and other objects are attained in accordance with the invention by the provision of a device for detecting fatigue of a monitored structure due to flexure, the monitored structure being made of a predetermined material and the device comprising: a fuse made of the predetermined material and formed with a failure portion designed to fail because of fatigue prior to failure of the monitored structure when the fuse and the monitored structure both experience the same stress history; and adhesive means securing the fuse to the monitored structure and extending substantially over the entirety of a side of the fuse that is adjacent to said monitored structure but being spaced apart from the failure portion; whereby the adhesive means ensures that the fuse and the monitored structure are subjected to substantially the same stress history in both tension and compression yet does not inhibit failure of the failure portion.

In accordance with an independent aspect of the invention, there is provided a device for detecting fatigue of a monitored structure due to flexure, the monitored structure being made of a predetermined material and the device comprising: a fuse made of the predetermined material and formed with a plurality of failure portions designed to fail because of fatigue prior to failure of the monitored structure when the fuse and the monitored structure both experience the same stress history; and adhesive means securing the fuse to the monitored structure; wherein the fuse is formed of an electrically conductive material and is divided into a plurality of legs, one leg corresponding to each of the failure portions; further comprising means for applying a voltage to the fuse and means responsive to signals in the legs; whereby failure of any of the legs can be detected by loss of a signal therein.

In accordance with another independent aspect of the invention, there is provided a method of applying a fatigue fuse formed with at least one failure portion to a structure to be monitored. Included among the steps of the method is the step of applying an adhesive substantially to the entirety of a side of the fuse to be placed adjacent to the monitored structure while maintaining the adhesive in spaced-apart relation to the failure portion. Preferably, a mask is applied to the failure portion before the step of applying the adhesive, thereby facilitating the maintaining of the spaced-apart relation A better understanding of the objects, features and advantages of the invention can be gained from a consideration of the following detailed description of the preferred embodiment thereof, in conjunction with the accompanying figures of the drawing, wherein a given reference character always refers to the same element or part.

DESCRIPTION OF THE PREFERRED EMBODIMENTS

Figure 2:
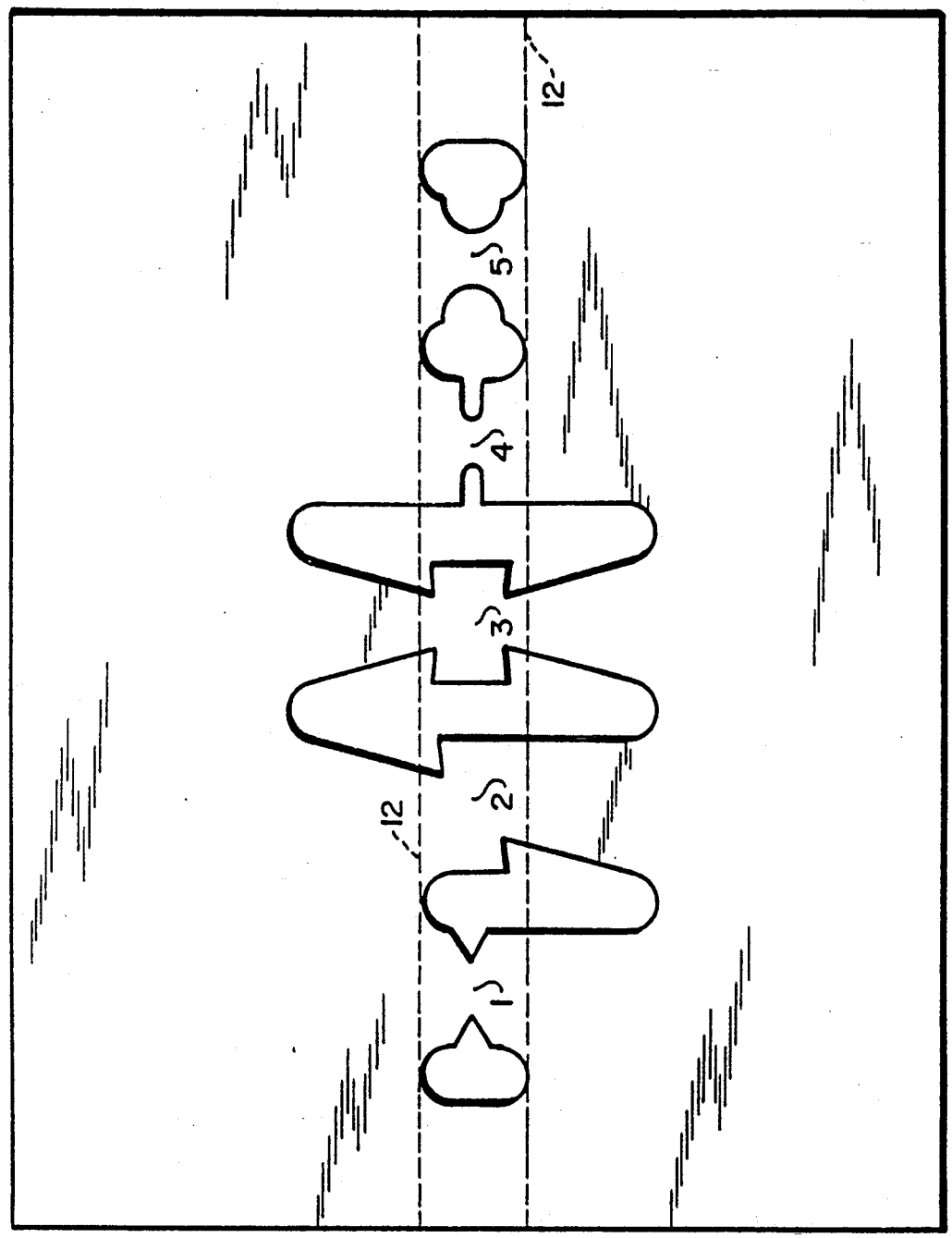
FIG. 2 is a plan view of a fatigue-detecting device constructed in accordance with the present invention and intended for visual inspection.

FIG. 2 shows a device for detecting fatigue of a monitored structure due to flexure, the monitored structure being made of a predetermined material. While the monitored structure is not illustrated, it can be a part of a bridge, ship, bulldozer, truck, mobile missile, gun mount, commercial electric power generator (nuclear or conventional), chemical plant, tower, crane, oil rig, airplane, etc. In an airplane, to take just one example, the part monitored can be an inboard or outboard stringer splice, a floor system, a wing-fuselage tee, a spar cap splice, etc. In general, the part monitored can be flat, concave, or convex. Typically, the predetermined material of which the monitored structure is made will be an aluminum alloy or a steel alloy, although it may be another metal, a plastic, or any other structural material subject to failure because of fatigue. The monitored structure and the fuse may be made, for example, of 7075 aluminum, 6061 aluminum, 2040 aluminum, 1018 mild steel, 31600 stainless steel, etc.

The device shown in FIG. 2 comprises a fuse 10 made of the same material as the monitored structure and formed with failure portions 1 through 5 indicated between dashed lines 12. The regions 1 through 5 are designed to fail because of fatigue in a predetermined sequence corresponding to the assigned reference numbers. The design of the failure portions 1 through 5 is such that the last to fail (portion 5) will fail well in advance of failure of the monitored structure during normal conditions of service. This assumes, of course, that the fuse 10 and the monitored structure both experience the same stress history.

In accordance with the invention, an adhesive secures the fuse 10 to the monitored structure and extends substantially over the entirety of the side of the fuse that is adjacent to the monitored structure but is spaced apart from the failure portions 1 through 5. The adhesive should make contact with the fuse over at least 75% and preferably at least 85% of the area of a side of the fuse adjacent to the monitored structure. If the fuse is designed for visual monitoring (FIG. 2), the adhesive should make contact with substantially 90% of the area of the side of the fuse adjacent to the monitored structure. The adhesive thus ensures that the fuse and the monitored structure are subjected to substantially the same stress history in both tension and compression. On the other hand, since the adhesive is spaced apart from the failure portions 1 through 5, it does not inhibit their timely failure.

In applying a new fuse 10 to a structure to be monitored, first the monitored structure is thoroughly cleaned of paint, grease, dirt, etc., so that the fuse can be bonded firmly to it. In order to ensure that the adhesive is spaced apart from the failure portions 1 through 5, a mask is preferably applied to the region 12 extending over all of the failure portions 1 through 5. The area of the mask ranges from 10% to 25% of the area of the fuse, in correspondence with the percentages given above. An adhesive is then applied over the entirety of one side of the fuse, including the mask. The mask protects the notches of the failure portions 1 through 5 from being reinforced by the adhesive. The adhesive is also preferably applied to the properly cleaned structure to be monitored. The fuse is then firmly pressed against the structure to be monitored in such a manner that the two layers of adhesive are joined firmly to each other and therefore the fuse 10 is joined firmly to the monitored structure.

It is essential that the fuse 10 experience as nearly as possible the same history as the monitored structure. Accordingly, if the monitored structure is uncoated and therefore exposed to the weather, ultraviolet radiation, etc., the fuse is also left uncoated. If on the other hand the monitored structure is coated by paint, etc., then a corresponding protective coating, which need not be identical to the coating of paint, etc., but from the standpoint of affording protection from the environment should be equivalent thereto, is applied to the fuse.

Figure 3:
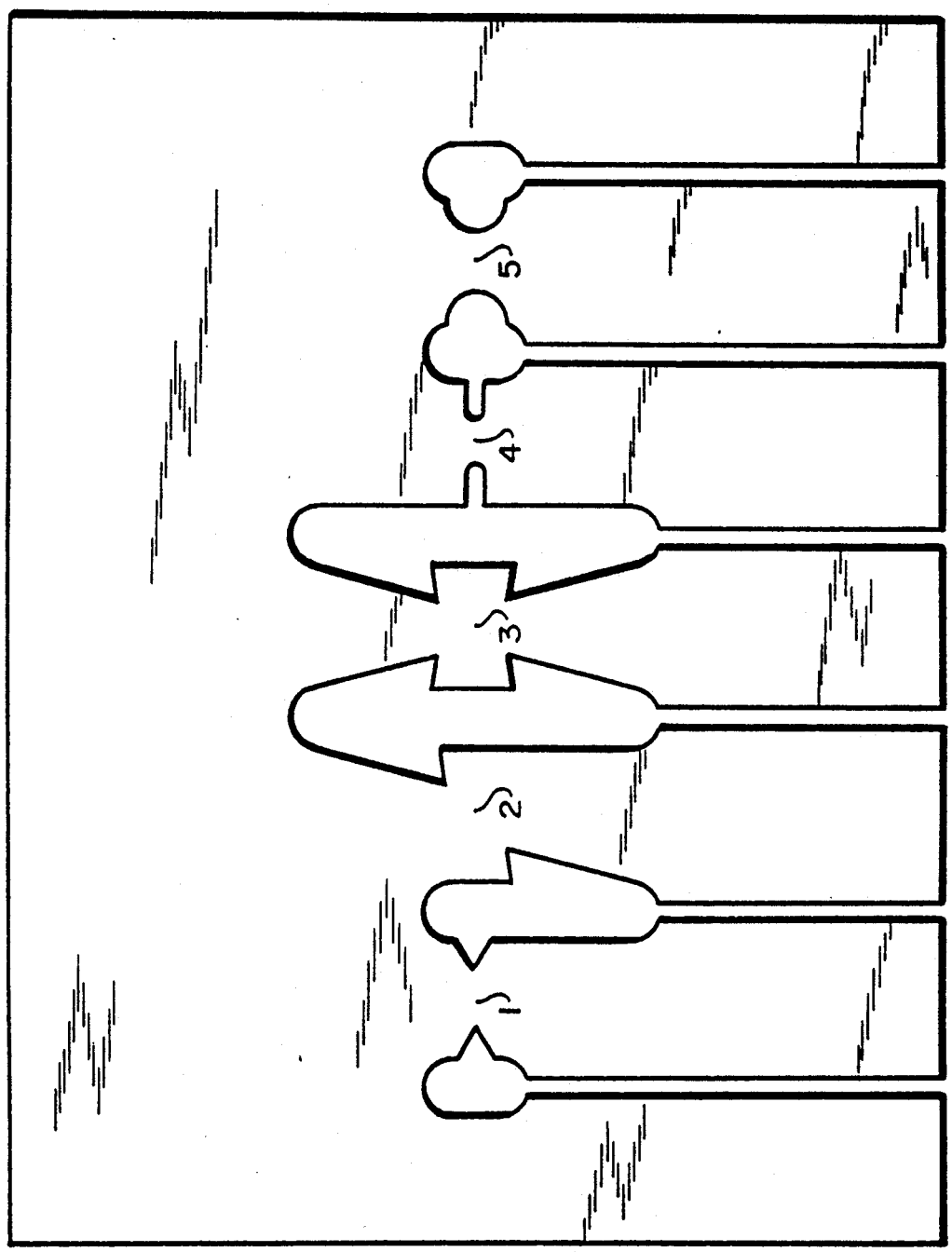
FIG. 3 is a plan view of a fatigue-detecting device constructed in accordance with the present invention and intended for remote monitoring.

FIG. 3 shows a fuse 10' adapted to a remote monitoring system. The fuse of FIG. 3 is like that of FIG. 2 except that the fuse of FIG. 3 is formed with six interruptions defining seven conductive legs forming parts of electrical circuits in parallel. A low positive potential is applied to the top of the fuse and current flows through each leg so long as that leg remains intact. As the failure portions 1 through 5 rupture sequentially, the legs change from a closed-circuit status to an open-circuit status, and this can be detected by an appropriate remote sensor. The leg to the left of the failure portion 1 and the leg at the right of the failure portion 5 may be employed or disregarded.

Figure 1:
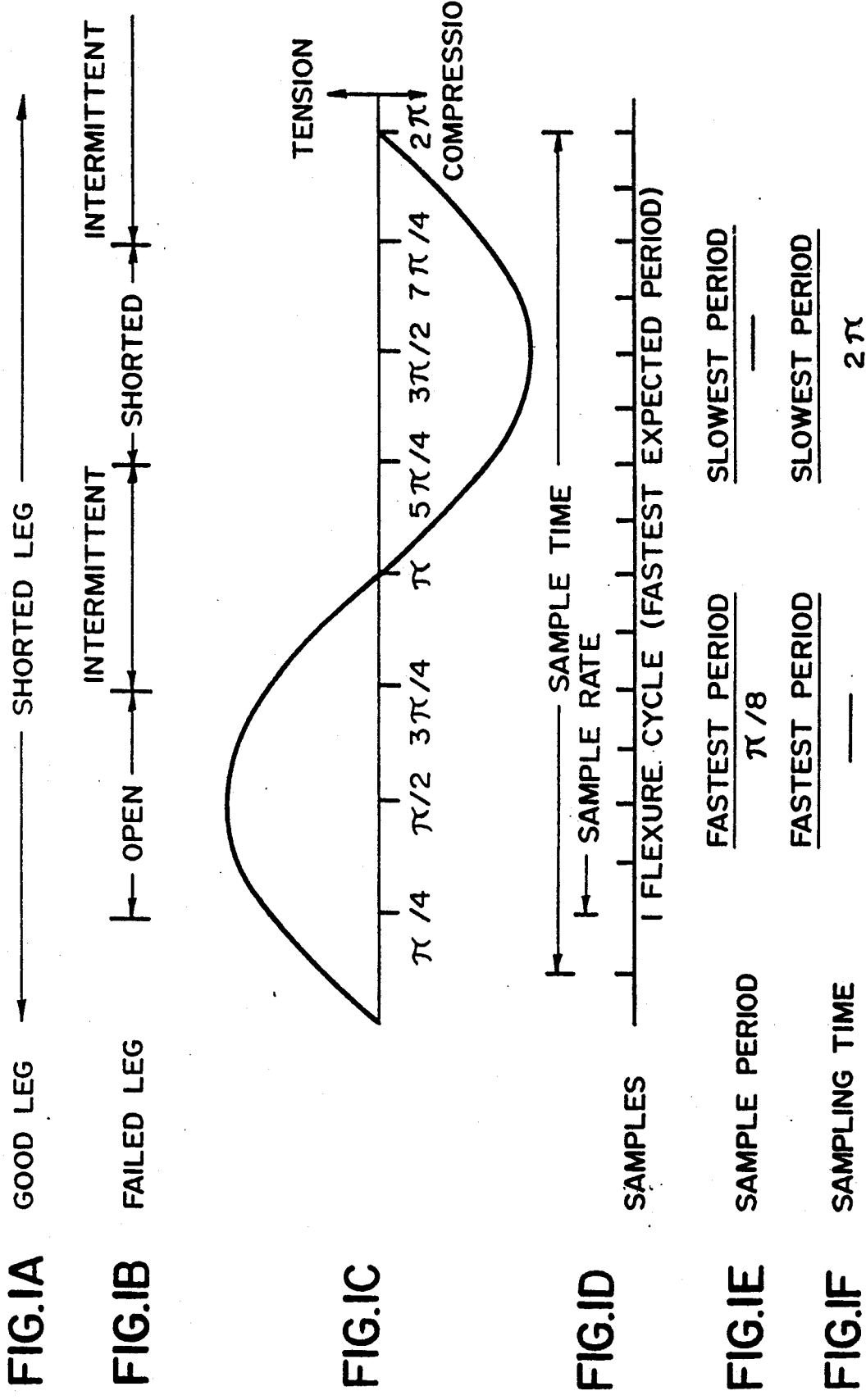
FIG. 1 (including parts A-F) is a graph showing the stress of a properly applied fatigue-detecting device during a stress cycle including both tension and compression.

FIG. 1 shows the fuse output when it is flexed and incorporated as part of a remote monitoring system. A good leg of the fuse is shorted, as indicated at line A of FIG. 1. A failed leg will typically be open in tension, intermittently open and shorted as it passes from tension to compression or vice versa, and shorted in compression, as indicated in lines B and C. One cycle of tension and compression extending from 0 to $2\pi$ radians is indicated in line C of FIG. 1, tension being indicated in the positive Y direction and compression in the negative Y direction. As indicated in lines D, E and F, samples are taken at a sample period and extending over a sampling time which are related, respectively, to the fastest and slowest periods (highest and lowest frequencies) to be expected. Specifically, the sample period is equal to $\pi/8$ times the fastest expected period, and the samples are taken over a sampling time equal to $2\pi$ times the slowest expected period. This ensures statistically reliable samples under all conditions to be encountered in normal service.

Figure 4:
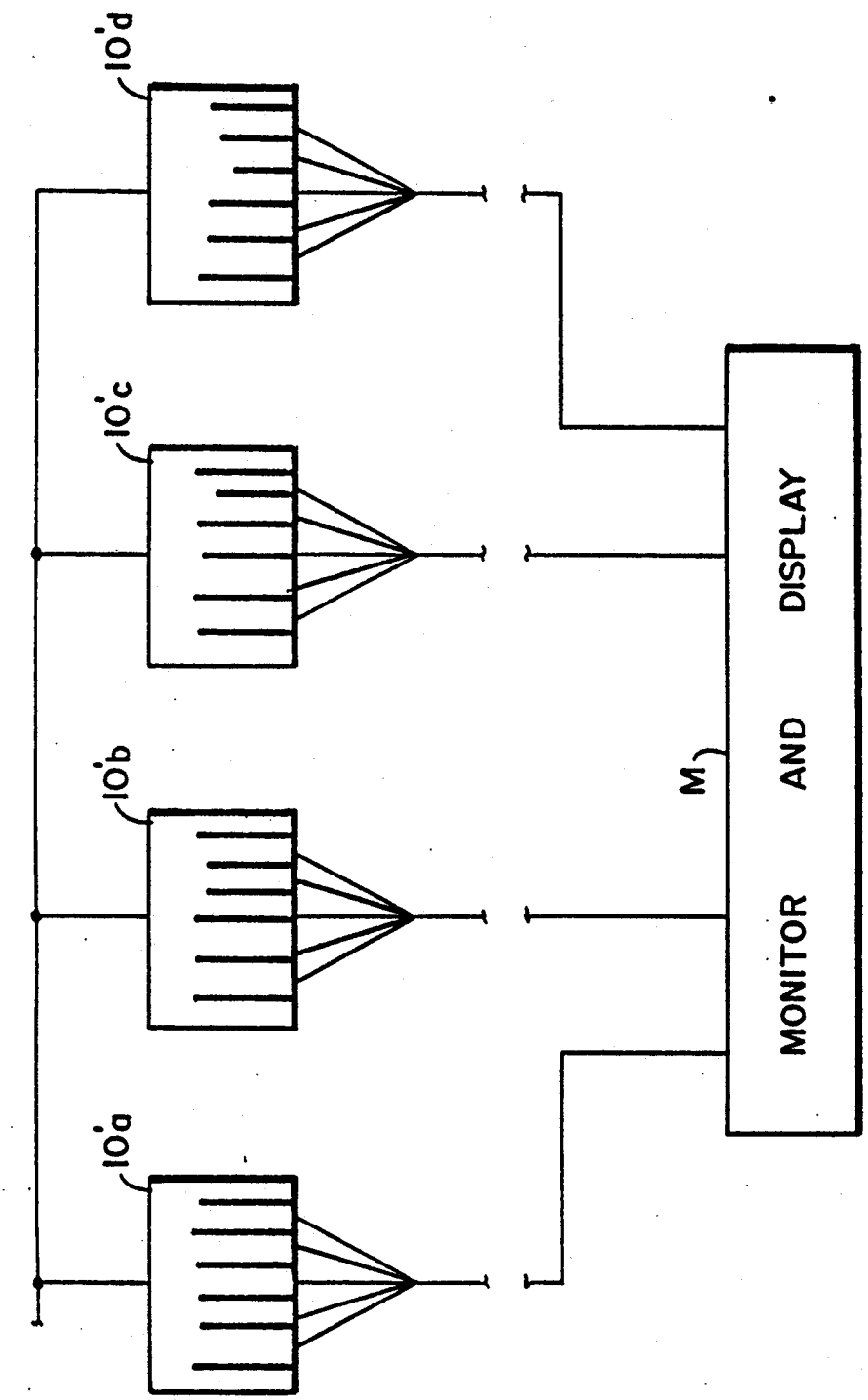
FIG. 4 illustrates schematically a remote monitoring system including devices constructed in accordance with the present invention.

FIG. 4 illustrates in a schematic way a remote conventional monitor M that receives signals from each leg of a plurality of fuses 10' each constructed in accordance with the embodiment of the invention shown in FIG. 3. The legs are distinguished and a display incorporated in the monitor M provides an indication of each failure as it occurs together with an identification of the failed portion. The indicator thus indicates either directly or inferentially the approximate remaining service life of the monitored structure.

In accordance with the invention, the adhesive employed equals or exceeds certain standards for adhesives set by the American Society for Testing and Materials (ASTM), particularly ASTM D1062, D1002, D950 and D1183. The test protocols, test equipment, and adhesive standards are set out in Section 15 of ASTM vol. 15-06 (1988), and results of tests made on a suitable adhesive are set out below. The adhesive must be strong, provide for equable transmission of stress and strain occurring in the structure to which it is bonded, be capable of operating in adverse environments while suffering no loss of strength or degradation of transmission of stress or strain, be easy to apply in the field, and, if the fuse is used for remote sensing, be non-conductive of electric currents and voltages so that the fatigue fuse can be used to transmit a signal to a remote location with no loss to the underlying structure. A suitable adhesive will meet the following ASTM performance characteristics.

Cleavage Strength of Metal-to-Metal Bonds (ASTM D1062)

This standard was applied to aluminum alloy and steel alloys and five specimens of each were tested under tension at a pull rate of 0.05" per minute.

The average for the aluminum alloy specimens was a break load of 11,800 lbs. of force with 95% in adhesive cohesion and 5% in adhesive contact. Since the fatigue fuse will fail, in all cases, at 30% of the above load (not psi) this adhesive strength has a 70% redundancy.

The average for the steel alloy specimen was a break load of 13,336 lbs. force, with 99% failure in adhesive cohesion and 0.8% in adhesive contact. This indicates even more cohesive strength than for the aluminum alloy and more tensile strength.

Strength Properties of Adhesives by Tension Loading (Metal-to-Metal) (ASTM D1002)

This test is to determine the comparative shear strength of adhesives for bonding metals. Ten specimens each of aluminum and steel alloy were tested in tension with the following results.

The aluminum alloy average tensile strength was 13,927 lbs. of force, with 98% of the adhesive failure mode in cohesion.

The steel alloy average tensile strength was 13,839 lbs. of force, with 99% of the adhesive failure mode in cohesion.

This tensile strength is far in excess of what is required for the fatigue fuse and ensures a wide safety margin.

Impact Strength of Adhesives (ASTM D950)

This test covers the determination of the impact value of adhesive bonds in shear.

Ten specimens each of aluminum and steel alloys were tested on an impact tester, with the following results:

The aluminum alloy average impact value was 292 ft-lbs/in$^2$ with adhesive failure mode at 98.8% in cohesion.

The steel alloy average impact value was 299.8 ft-lbs/in$^2$ with adhesive failure mode at 98.6% in cohesion.

These values greatly exceed the fatigue fuse requirements.

Fatigue Tests With Max Planck Adhesive

An adhesive was obtained from the Max Planck Institute in Stuttgart, Germany. This adhesive, referred to as the MP adhesive, was tested as follows:

Methodology for Fatigue Tests of the MP Adhesive

The purpose of these tests is to subject the MP adhesive to dynamic fatigue conditions, varying the stresses applied, in both tension and compression, and varying the test vibration frequency. Some of the tests are done off-axis, that is, the specimen is deliberately misaligned with the grips, the purpose being to induce a bending moment. The program to be followed is dictated by the result initially achieved in the LCF tests.

Since the purpose of the tests is to qualify the adhesive, fuses are not used for these tests, but specimens are made up of flat, unmarked Al 7075 and Fe 1020 sheets, of the same dimensions as the fatigue fuse, but of a thickness of 0.025" to allow higher stresses to be applied to the adhesive. These are then bonded with the MP adhesive to test beams of 0.50" thickness. Highest stresses to be applied do not exceed 60 Ksi (thousands of pounds per square inch) in tension and compression, and the tests are stopped at 1,000,000 cycles. There should be no failure of the dummy specimen at this load but it is estimated that there should be some plastic deformation and therefore some type of deformation of the adhesive. Should there be no failure of the adhesive at these stresses, the specimens are then sectioned at five intervals and the adhesive edge examined under a scanning electron microscope.

Fatigue test results at 30 and 40 Ksi, and at frequencies of up to 50 cycles per second are very positive, with no delamination of the adhesive being observed, even in the presence of a small bending moment. Scanning electron microscopy studies at the end of each test reveal no voids in the adhesive layers larger than 120 Angstrom units, and these are believed to have adhesive layers larger than 120 Angstrom units and these are believed to have occurred in the curing process rather than being due to fatigue stresses.

The conclusion reached is that the adhesive exhibits superior properties, far in excess of the loads to which it will be subjected in fatigue fuse applications.

Strength Properties at Elevated Temperature (+315° C.)

Ten specimens each of aluminum and steel alloys were pulled in tension at a rate of 1,400 psi per minute, at a temperature of 315° C. (600° F.).

The aluminum alloy parting load average was 12,294 psi, with the average time to failure being 8 minutes.

The steel alloy parting load was 10,911 psi, with the average time to failure being 7.5 minutes.

All specimens failed in cohesion, and the 15% decrease in strength from that tested at room temperature is attributed to the voids introduced in the adhesive by a thermocouple embedded to monitor adhesive temperature.

Strength Properties at Low Temperatures (−185° C.)

Ten specimens each of aluminum and steel alloys were pulled in tension at a rate of 1,400 psi per minute, at a temperature of −185° C.).

The cooling medium used was gaseous carbon dioxide.

The aluminum alloy parting load average was 11,641 psi, with the average time to failure being 8 minutes.

The steel alloy parting load was 11,026 psi, with the average time to failure being 8 minutes.

All specimens failed in cohesion, and the 18% decrease in strength from that tested at room temperature is attributed to the voids introduced in the adhesive by a thermocouple embedded to monitor adhesive temperature.

Resistance to Cyclic Laboratory Aging Conditions (ASTM D1183)

This series of tests exposes specimens to a series of high and low relative humidities and simulates accelerated service conditions. Salt water immersion and conditioning prepares the specimens for tensile tests to observe any possible deterioration of adhesive strength after such exposure.

The aluminum alloys specimens failed at an average of 13,412 lbs. of force, indicating a −0.4% change in strength as compared to specimens tested at room temperature and humidity.

The steel alloy specimens failed at an average of 11,755 lbs. of force, indicating a 0.86% change in strength as compared to specimens tested at room temperature and humidity.

Since these very small changes are well within the range of normal data scatter for tensile tests, it is concluded that no adverse effects were observed in salt water immersion.

Tests for Water Absorption

This series of tests functions to determine the proportion of water absorbed by the material and as a control test on the uniformity of the adhesive. The moisture content is intimately related to such properties as electric insulation, resistance, dielectric losses, mechanical strength, appearance and dimensions.

The tests resulted in the conclusion that there was a 0.0035% increase in weight (0.001 grams) and that no soluble matter was lost. No warping or distortion of the material was observed, and the minimal increase in weight falls well within the expected accuracy of the measurement instruments used.

It is concluded that there was no loss of electrical non-conductivity properties.

Deflection Temperature of the Adhesive Under Flexural Load

A uniform stress of 264 psi is applied to an adhesive specimen immersed in a heat transfer medium that gradually heats the specimen. The temperature at which the specimen deflects 0.010" is recorded.

Specimen No. 1 deflected 0.010" at a temperature of 246° F. and specimen No. 2 deflected equally at a temperature of 262° F.

The conclusion reached is that the adhesive will not deflect away, or impose additional stress or strain on the fatigue fuse, when subjected to flexural loads and temperatures considerably beyond those likely to be experienced by the fatigue fuse.

As noted above, a suitable adhesive meeting the characteristics set out above is available from the Max Planck Institute in Stuttgart, Germany. Other suitable adhesives such as five-minute or quick-drying structural epoxies are described in various U.S. patents and are available from various commercial sources.

Thus in accordance with the invention a novel and highly effective device for detecting fatigue of a monitored structure due to flexure and a method of applying the device to the monitored structure are provided. The invention remedies the problems of the prior art noted above and provides a fatigue monitor that more reliably gives warning of impending failure of a monitored structure. In particular, there is provided in accordance with the invention a fatigue monitor that more faithfully mirrors the stress history of the monitored structure, especially in compression. Moreover, a fatigue monitor in accordance with the invention is ideally adapted for incorporation in a remote monitoring system.

Many modifications of the preferred embodiments of the invention described above will readily occur to those skilled in the art upon consideration of this disclosure. For example, the shape of the notches is not critical, and in fact failure portions otherwise weakened so as not to depend on the provision of notches can be employed. The number of failure portions is also not critical, and the design of the remote monitoring electronic equipment can easily be varied to suit the installation. The nature of the adhesive is not critical so long as it meets the chemical and physical requirements set out above. Accordingly, the invention is not limited except by the appended claims.

I claim:

1. A device for detecting fatigue of a monitored structure due to flexure, said monitored structure being made of a predetermined material and said device comprising:
   a substantially flat integral fuse made of said predetermined material and having edges and a plurality of differently configured cut out portions between the edges and defining fuse elements therebetween designed to fail because of fatigue prior to failure of said monitored structure when said fuse and said monitored structure both experience thee same stress history;
   means forming parallel elongated slots extending from the cut out portions to one edge to define legs associated with the fuse elements;
   adhesive means securing said fuse to said monitored structure and extending over at least 75% of the area of the side of said fuse that is adjacent to said monitored structure but being spaced apart from said fuse elements;

whereby said adhesive means ensure that said fuse and said monitored structure are subjected to substantially the same stress history in both tension and compression yet does not inhibit failure of said fuse elements.

2. A device according to claim 1 wherein said predetermined material is a metal.

3. A device according to claim 1 wherein said failures occur substantially at different predetermined percentages of the expected life of said monitored structure.

4. A device according to claim 1 wherein said percentage is at least 85%.

5. A device according to claim 1 wherein said fuse is designed for visual monitoring and said percentage is substantially 90%.

6. A device for detecting fatigue of a monitored structure due to flexure, said monitored structure being made of a predetermined material and said device comprising:

a substantially flat integral fuse made of said predetermined material and having edges and a plurality of differently configured cut out portions between the edges and defining fuse elements therebetween designed to fail because of fatigue prior to failure of said monitored structure when said fuse and said monitored structure both experience the same stress history;

adhesive means securing said fuse to said monitored structure;

wherein said fuse is formed of an electrically conductive material and has means forming parallel elongated slots extending from the cut out portions to the edge to define legs associated with the fuse elements; and further comprising means for applying a voltage to said fuse and means responsive to signals in said legs;

whereby failure of any of said legs can be detected by loss of a signal therein.

7. A method of applying a fatigue fuse formed with at least one failure portion to a structure to be monitored for fatigue by said fatigue fuse, said method comprising the steps of applying an adhesive over at least 75% of the area of a side of said fuse to be placed adjacent to said monitored structure while maintaining said adhesive in spaced-apart relation to said failure portion by applying a mask to the failure portion before applying adhesive; and applying said fuse to said structure to be monitored.

8. A method according to claim 7 further comprising, as a separate step, applying said adhesive to said structure to be monitored.

9. A device for monitoring the fatigue life of a structural member composed of a predetermined material, the device comprising: a substantially flat integral fuse composed of said predetermined material and mountable on a structural member during use, said fuse having edges and a plurality of differently configured cut out portions between the edges defining a fuse element between each pair of adjacent cut out portions, wherein each fuse elements has a different shape configured to fail at different times in sequence because of fatigue and prior to the failure of the monitored structural member when the fuse and the monitored structural member are subjected to substantially the same stress history and wherein the cut out portions include parallel elongated slots extending to one edge to define legs associated with the fuse elements.

10. The device according to claim 9, wherein the predetermined material is a metal.

11. The device according to claim 10, further comprising monitoring means electrically connected to each of the legs for detecting a failure in each fuse element.

12. The device according to claim 9, wherein the fuse has a rear surface configured to permit at least 75% to be adhered to the monitored structural member.

13. The device according to claim 9, wherein the fuse has a rear surface configured to permit up to 90% to be adhered to the monitored structural member.

14. A method for monitoring the fatigue life of a structural member composed of a predetermined material, the method comprising: providing a substantially flat integral fuse composed of said predetermined material and having edges and two main surfaces, said fuse having a plurality of differently configured cut out portions between the edges defining a fuse element between each pair of adjacent cut out portions, wherein each fuse element has a different shape configured to fail at different times in sequence because of fatigue and prior to the failure of the monitored structural member when the fuse and the monitored structural member are subjected to substantially the same stress history, providing cut out portions with parallel elongated slots extending to one edge to define legs associated with the fuse elements and mounting the fuse on the structural member by applying adhesive to at least 75% of one main surface of the fuse.

15. The method according to claim 14, further comprising electrically monitoring each of the legs for detecting a failure in each fuse element.

16. The method according to claim 14, wherein the fuse is mounted by applying adhesive on up to 90% of the one main surface.

* * * * *